United States Patent
Ries et al.

(10) Patent No.: US 8,608,744 B2
(45) Date of Patent: Dec. 17, 2013

(54) METHODS AND APPARATUS FOR ACETABULAR ARTHROPLASTY

(75) Inventors: Michael D. Ries, Tiburon, CA (US); David C. Kelman, Collierville, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 13/132,286

(22) PCT Filed: Dec. 2, 2009

(86) PCT No.: PCT/US2009/066462
§ 371 (c)(1),
(2), (4) Date: Aug. 12, 2011

(87) PCT Pub. No.: WO2010/065677
PCT Pub. Date: Jun. 10, 2010

(65) Prior Publication Data
US 2011/0306978 A1 Dec. 15, 2011

Related U.S. Application Data (60) Provisional application No. 61/119,210, filed on Dec. 2, 2008.

(51) Int. Cl.
*A61B 17/16* (2006.01)

(52) U.S. Cl.
USPC .......................................................... 606/79

(58) Field of Classification Search
USPC ................... 606/86 R, 79–85, 95, 99, 102; 623/22.11–22.29
See application file for complete search history.

(56) References Cited

U.S. PATENT DOCUMENTS

| | | | |
|---|---|---|---|
| 5,879,353 A | 3/1999 | Terry | |
| 6,106,536 A | 8/2000 | Lechot | |
| 6,319,256 B1 | 11/2001 | Spotorno et al. | |
| 6,368,324 B1 | 4/2002 | Dinger et al. | |
| 6,997,928 B1 | 2/2006 | Penenberg | |
| 7,833,229 B2 * | 11/2010 | Penenberg | 606/81 |
| 8,211,183 B2 * | 7/2012 | Podolsky | 623/22.15 |
| 2006/0129159 A1 | 6/2006 | Lee | |
| 2008/0195221 A1 * | 8/2008 | Howald et al. | 623/22.32 |

FOREIGN PATENT DOCUMENTS

CN 1230391 A 10/1999

OTHER PUBLICATIONS

Search Report; Chinese Patent Application No. 200980156364.6; Jun. 7, 2013; 5 pages.
First Office Action; Chinese Patent Application No. 200980156364.6; Jun. 20 2013; 8 pages.

* cited by examiner

*Primary Examiner* — Kevin T Truong
*Assistant Examiner* — Christopher Beccia
(74) *Attorney, Agent, or Firm* — Krieg DeVault LLP (57) ABSTRACT

A method for performing an acetabular arthroplasty in an acetabulum of an ilium may include locating an iliac canal of the ilium. The iliac canal extends from the surface of the acetabulum generally toward a portion of the iliac ridge. An impacting step impacts a non-rotating bone removal tool aligned along the iliac canal such that the non-rotating bone removal tool removes bone within the iliac canal and forms a bone void. Another step secures a fixation implant within the canal void. An acetabular implant is installed within the acetabulum over the fixation implant.

22 Claims, 9 Drawing Sheets

METHODS AND APPARATUS FOR ACETABULAR ARTHROPLASTY

CROSS-REFERENCE TO RELATED APPLICATIONS

This application is a United States National Phase filing of International Application No. PCT/us2009/066462 filed Dec. 2, 2009, which claims the benefit of U.S. Provisional Application No. 61/119,210, filed Dec. 2, 2008 and titled "Iliac Canal Prosthesis". The disclosure of these applications are incorporated by reference in their entirety.

BACKGROUND OF THE INVENTION

1. Field of the Invention

The present invention relates generally to methods of preparing acetabular bone for securing acetabular implants, and more particularly to a method of preparing an acetabulum using non-rotating cutting means. Moreover, the invention relates to a method of securing acetabular augments to the canal of the ilium using broaches and rasps.

2. Related Art

In the past, the iliac canal has been utilized for fixedly securing an artificial acetabular bearing surface to pelvic bone. Such prostheses utilized a screw stem attached to a cup having an articulating surface thereon and were referred to in the art as "Ring prostheses". Ring prostheses were generally monolithic, and made of metal. Uncemented polyethylene-on-metal (UPM) hip prostheses have also utilized fixation to the iliac canal. The UPM hip prosthesis was a successor to the all-metal Ring prosthesis described above.

To this end, all current acetabular prostheses utilizing the iliac canal for fixation do not provide a surgeon with modularity, intraoperative options, and/or material choices. Moreover, the prior art methods of acetabular preparation for such acetabular prostheses utilizing the iliac canal for fixation required rotating cutting means such as a hemispherical reamer, drill bit, reamer, or screw.

SUMMARY OF THE INVENTION

The aforementioned needs are satisfied by several aspects of the present invention.

According to an aspect of the invention, there is provided a method of preparing an acetabular region for the acceptance of an acetabular implant configured to engage at least a portion of the intramedullary canal of an ilium. The method comprises the step of using at least one non-rotating means for bone removal to prepare an intramedullary surface of an ilium for acceptance of said acetabular implant. The implant may be, for example, a stem portion of an acetabular prosthesis, or an augment for encouraging acetabular prosthesis stability.

According to other aspects of the invention, there are provided surgical instruments for preparing a portion of the intramedullary canal of an ilium bone. The surgical instruments provided may be configured as broaches or rasps which serve as non-rotating means for ilium bone removal.

According to yet another aspect of the invention, a method for performing an acetabular arthroplasty in an acetabulum of an ilium is provided. The method may include locating an iliac canal of the ilium. The iliac canal extends from the surface of the acetabulum generally toward a portion of the iliac ridge. An impacting step impacts a non-rotating bone removal tool aligned along the iliac canal such that the non-rotating bone removal tool removes bone within the iliac canal and forms a bone void. Another step secures a fixation implant within the canal void. An acetabular implant is installed within the acetabulum over the fixation implant.

Another aspect provides the locating step may comprise the step of cannulating the iliac canal.

According to another aspect, the locating step may comprise positioning a canal finding jig over the ilium.

According to yet another aspect, the canal finding jig may comprise a first portion, a second portion and an alignment guide. The positioning a canal finding jig step further comprises positioning the first portion of the canal finding jig against a portion of the acetabulum and positioning the second portion of the canal finding jig against a portion of the iliac ridge such that the alignment guide is aligned along an axis of the iliac canal.

Yet another aspect may further comprise creating a bone void surrounded by cortical bone.

According to another aspect, the impacting step may further comprise impacting a plurality of non-rotating bone removal tools.

According to yet another aspect, the impacting step may further comprise impacting a plurality of differently sized non-rotating bone removal tools.

The securing step may further comprise the step of cementing the fixation implant into the canal void in yet another aspect.

According to another aspect, the acetabular implant may be an acetabular cup.

According to yet another aspect, the acetabular component may be an acetabular cage.

Another aspect provides a non-rotating bone removal tool for an iliac canal. The tool may include a bone removing surface configured to remove bone from the iliac canal and form a bone void. A positioning portion may be configured to position the bone removing surface within the iliac canal. The bone removing surface may be configured relative to the positioning portion such that the bone removing surface creates a bone void within the iliac canal such that the bone removing surface abuts cortical bone.

In yet another aspect, the positioning portion may be a hollow portion configured to receive a cannula.

According to another aspect, the bone removing surface may be formed from a preoperative image.

According to yet another aspect, the bone removing surface may be formed from a plurality of parts joined together forming an irregular shape.

In yet another aspect, the bone removing tool may comprise a plurality of modular removable surfaces such that each modular removable surface may be attached to the non-rotating bone removal tool independently. The bone void is formed by the combination of the plurality of modular removable surfaces formed in a series of impacting steps.

Further areas of applicability of the present invention will become apparent from the detailed description provided hereinafter. It should be understood that the detailed description and specific examples, while indicating certain embodiment of the invention, are intended for purposes of illustration only and are not intended to limit the scope of the invention.

BRIEF DESCRIPTION OF THE DRAWINGS

The accompanying drawings, which are incorporated in and form a part of the specification, illustrate the embodiments of the present invention and together with the written description serve to explain the principles, characteristics, and features of the invention. In the drawings.

DETAILED DESCRIPTION OF THE EMBODIMENTS

The following description of the preferred embodiment(s) is merely exemplary in nature and is in no way intended to limit the invention, its application, or uses.

The invention provides, in part, a method of preparing an acetabular region for acceptance of an acetabular implant, particularly a porous augment or a prosthesis utilizing the iliac canal as a stable anchor or as a means for proper orientation. Methods of the present invention utilize the iliac canal as an intact, repeatably identifiable anatomical landmark which can be used to orient and/or mount an acetabular implant with a relatively high degree of confidence. Where used herein, "acetabular implant" may include any one or more of the following, without limitation: a porous metal, a porous augment, a semi-porous augment, a non-porous augment, an acetabular cage, an acetabular shell, an acetabular liner, or devices or portions thereof which are configured for implantation in or around acetabular bone. The methods of the present invention are especially advantageous for use with implants having a stem portion configured for insertion into the prepared iliac canal, essentially forming a "foundation" for building up lost or compromised bone. It is preferred that cementless implant options be utilized where possible, however, acetabular implants of the present invention may incorporate cemented options.

The usefulness of the present invention is not limited to acetabulum, but may also have some practicality in shoulder arthroplasty (e.g., instances of trauma).

Figures 1A, 1B, 1C, 1D, 1E, 1F, 1G, 1H, 1I, 1J:
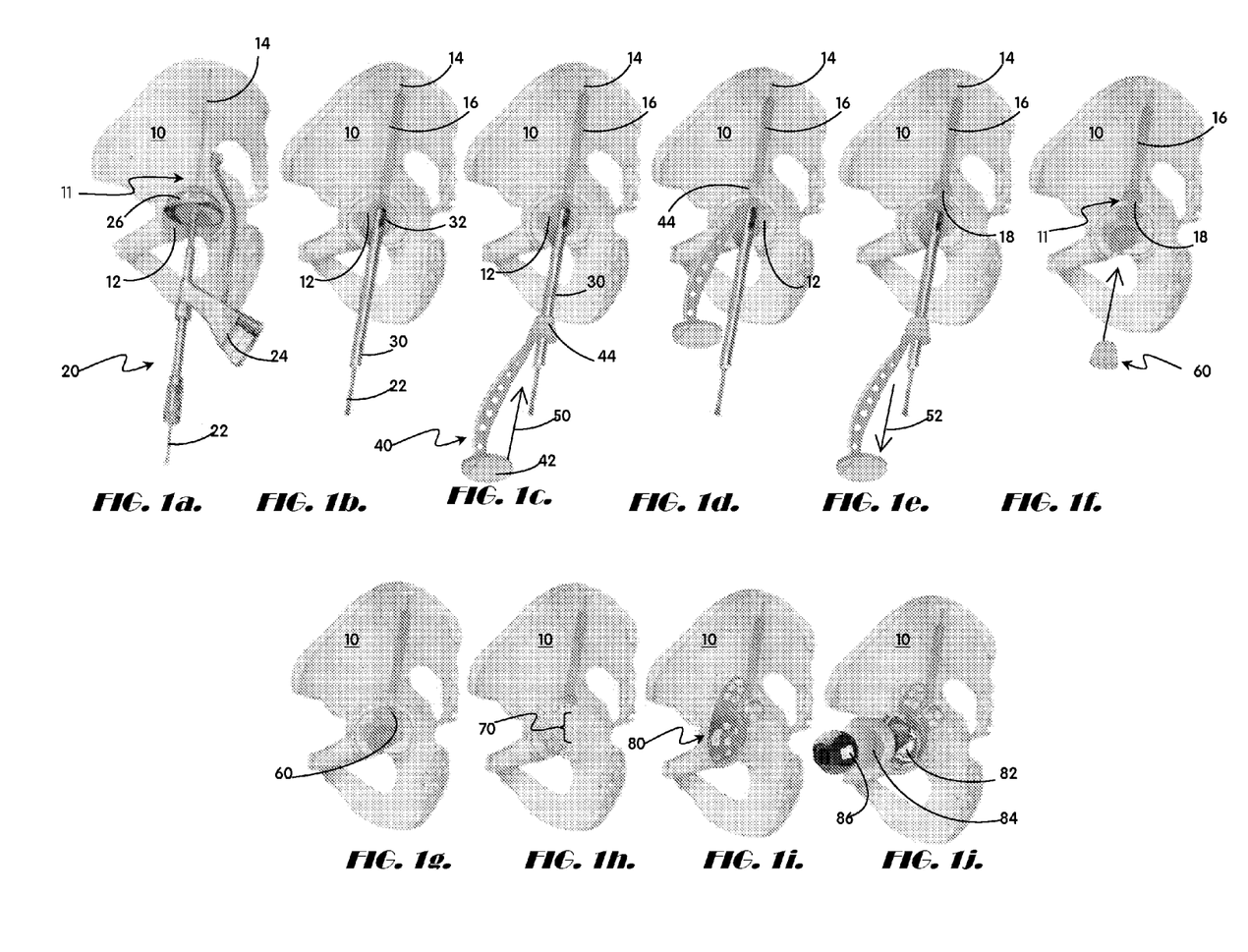
FIGS. 1a-1j illustrate a method of preparing an acetabular region according to one embodiment.

FIGS. 1a-1j illustrate a method of preparing an acetabular region according to one embodiment. Turning to FIG. 1a, the acetabulum 12 of an ilium bone 10 is provided. A canal-finding cannula 22, which in this embodiment is a guide rod, but may otherwise be a pin or a reamer, or some other directional tool extending within the iliac canal, is positioned in the canal 11 of the ilium 10 via a guide rod inserter jig 20. The guide rod inserter jig may have a handle 24 for holding, and a positioning end 26 which is received in the acetabulum 12.

The jig 20 is moved in circular fashion until the guide rod 22 is aligned with the intramedullary canal 11 of the ilium 10. The guide rod 22 is then inserted into the intramedullary canal 11 using impact force, or by providing a self-drilling tip 14 on the guide rod 22. Alternatively, the jig 20 may be used to pre-drill for the guide rod 22 in a separate step.

FIG. 1b illustrates the step of reaming over the guide rod 22 using a cannulated reamer 30 which slides over the guide rod 22. While not shown in the drawings, the reamer 30 need not be cannulated if a guide rod 22 is not used. In such instances, a surgeon would simply orient the reamer, ream, and leave the reamer in situ within the intramedullary canal 11. Reamer 30 has cutting surfaces 16 which help open up the iliac canal 11 by removing bone. A series of reamers 30 having different diametrical sizes may be provided to accommodate different patients, and depth marking indicia may be provided thereon to indicate depth of bone removal.

After reaming is complete, non-rotating means for ilium bone removal such as a cannulated broach or rasp 44 may be placed over the reamer 30 as illustrated in FIG. 1c. The broach 44 is connected to or made integral with a broach handle 40 having an impaction surface 42 as is conventionally done for femoral and humeral stem broaches. Whilst not shown in the drawings, the broach 44 need not be cannulated if guide rods 22 and reamers 30 are not used (e.g., instances of osteoporotic bone). A series or set of broaches 44 having different geometries and sizes may be provided to accommodate different patients, unique cases, and/or left or right acetabular regions as will be discussed hereinafter.

The broach 44 is impacted into the iliac canal 11 whilst being guided by the guide rod 22 and reamer 30. Radial orientation of the broach 44 relative to the reamer 30 and rod 22 is generally made before impaction 50. After impaction 50, the broach 44 is removed from the canal 11 via an extraction force 52 applied to the broach 44 or broach handle 40 as shown in FIG. 1e. Removal of the broach 44 creates a bone void 18 in the ilium 10 configured to receive a predetermined acetabular implant 60. Implant 60 may be, for example, a stem of an acetabular prosthesis or a porous augment as shown in the drawings. Void 18 is preferably created within the confines of the iliac canal 11, and is preferably bound by inner cortical bone of the ilium 10 exposed by the broach 44. Implant 60 is then inserted into the void 18 and secured by friction fit or cement. A separate impactor (not shown) or the broach handle 40 may help in securing the implant 60 within the void 18.

Next, an acetabular component 80 such as an acetabular cage, shell 82, or liner 84 is provided and installed over the implant 60. In some embodiments, it may be desirable to provide bone cement and/or bone graft materials 70 to the prepared acetabular region. Alternatively to, or in combination with cement and/or bone graft materials 70, cancellous screws, cortical screws, pegs, wires, or cables (not shown) may be used to further secure acetabular components 80, 82, 84 to the acetabular region.

Figures 2A, 2B, 2C, 2G, 2H:
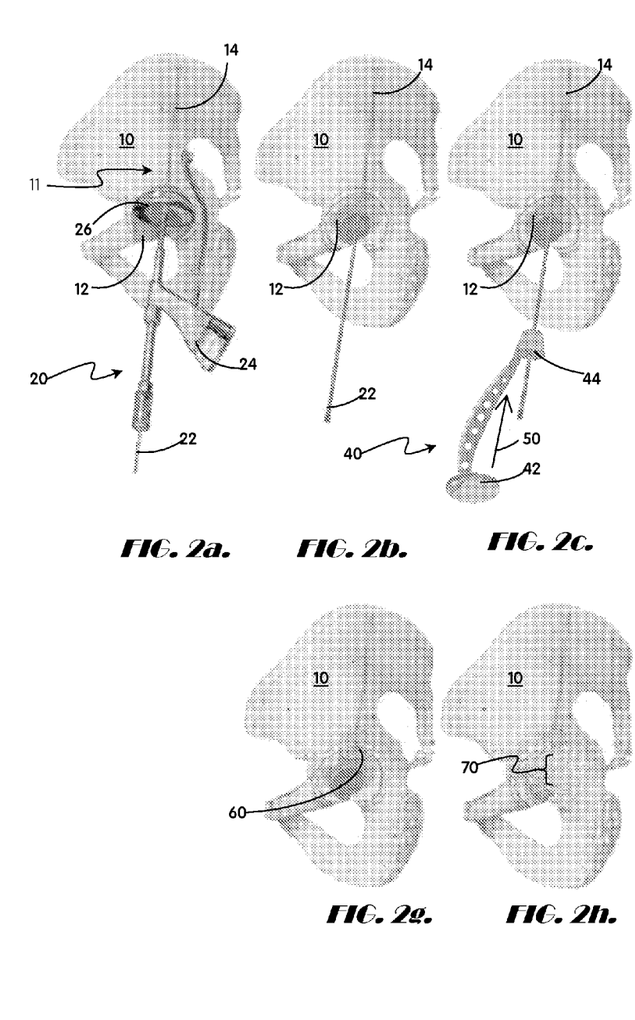
FIGS. 2a-j. illustrate a method of preparing an acetabular region according to another embodiment.
Figure 2D:
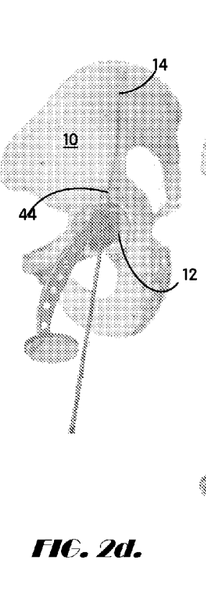

FIGS. 2*a-j*. illustrate a method of preparing an acetabular region according to another embodiment. Turning to FIG. 2*a*, the acetabulum 12 of an ilium bone 10 is provided. A canal-finding guide rod 22 is positioned in the canal 11 of the ilium 10 via a guide rod inserter jig 20. A series of guide rods 22 having different diametrical sizes may be provided to accommodate different patients, and depth marking indicia may be provided thereon to indicate depth of bone removal. The guide rod inserter jig may have a handle 24 for holding, and a positioning end 26 which is received in the acetabulum 12. The jig 20 is moved in circular fashion until the guide rod 22 is aligned with the intramedullary canal 11 of the ilium 10. The guide rod 22 is then inserted into the intramedullary canal 11 using impact force, or by providing a self-drilling tip 14 on the guide rod 22. Alternatively, the jig 20 may be used to pre-drill for the guide rod 22 in a separate step. FIG. 2*b* illustrates the step of removing the jig 20 and leaving the guide rod 22 in-situ.

After guide rod insertion is complete, non-rotating means for ilium bone removal such as a cannulated broach or rasp 44 may be placed over the guide rod 22 as illustrated in FIG. 2*c*. The broach 44 is connected to or made integral with a broach handle 40 having an impaction surface 42 as is conventionally done for femoral and humeral stem broaches. Whilst not shown in the drawings, the broach 44 need not be cannulated if guide rod 22 is not used (e.g., instances of osteoporotic bone). A series or set of broaches 44 having different geometries and sizes may be provided to accommodate different patients, unique cases, and/or left or right acetabular regions as will be discussed hereinafter.

Figure 2E:
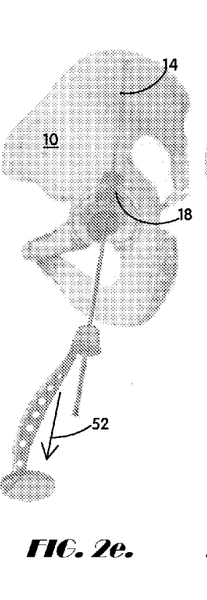
Figure 2F:
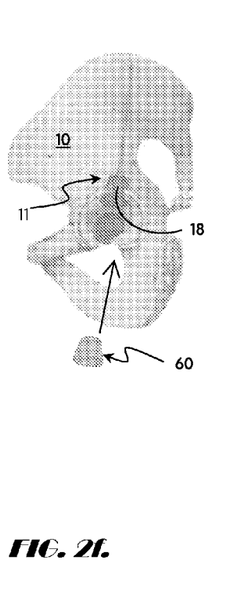
Figure 2I:
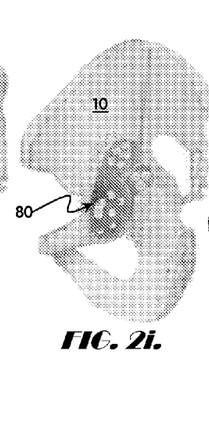
Figure 2J:
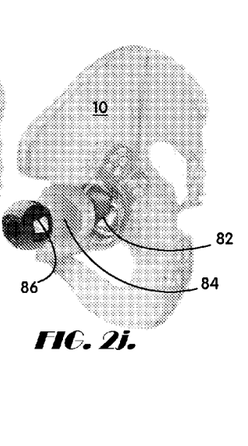

The broach 44 is impacted into the iliac canal 11 whilst being guided by the guide rod 22. Radial orientation of the broach 44 relative to the reamer 30 and rod 22 is generally made before impaction 50. After impaction 50, the broach 44 is removed from the canal 11 via an extraction force 52 applied to the broach 44 or broach handle 40 as shown in FIG. 2*e*. Removal of the broach 44 creates a bone void 18 in the ilium 10 configured to receive a predetermined fixation implant 60. Implant 60 may be, for example, a stem of an acetabular prosthesis or a porous augment as shown in the drawings. Void 18 is preferably created within the confines of the iliac canal 11, and is preferably bound by inner cortical bone of the ilium 10 exposed by the broach 44. Implant 60 is then inserted into the void 18 and secured by friction fit or cement. A separate impactor (not shown) or the broach handle 40 may help in securing the implant 60 within the void 18.

Next, an acetabular component 80 such as an acetabular cage, shell 82, or liner 84 is provided and installed over the implant 60. In some embodiments, it may be desirable to provide bone cement 70 to the prepared acetabular region. Alternatively to, or in combination with cement 70, cancellous screws, cortical screws, pegs, wires, or cables (not shown) may be used to further secure acetabular components 80, 82, 84 to the acetabular region.

Figure 3:
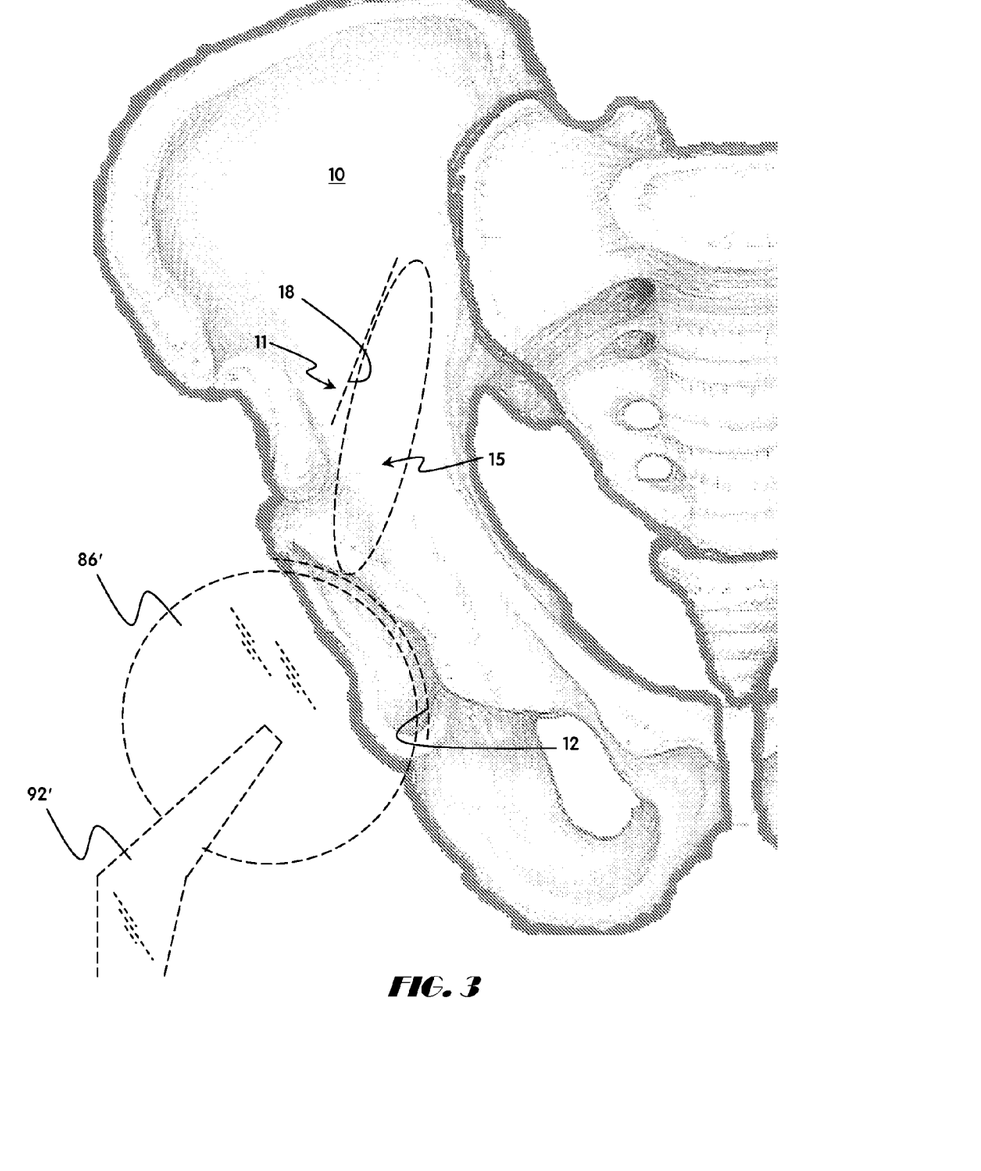
FIG. 3 is a frontal coronal view of a partially reconstructed hip showing the iliac canal area of the ilium and a pre-existing femoral implant.

FIG. 3 is a frontal coronal view showing the iliac canal area of the ilium. Shown, is schematic diagram illustrating an example of a pre-operative patient condition prior to implantation of an acetabular prosthesis according to the methods of the present invention. A pre-existing femoral head prosthesis 86' articulates with worn natural cartilage of an acetabulum 12 (i.e., hip hemi-arthroplasty). A fixation portion 15 of the iliac canal 11 of the ilium 10 is shown just superior to the femoral head prosthesis 86'. An acetabular implant size and geometry is selected based on preoperative templating, while keeping in consideration, press-fit quality with interior surfaces 18 of the intramedullary canal 11 of the ilium 10.

Figure 4:
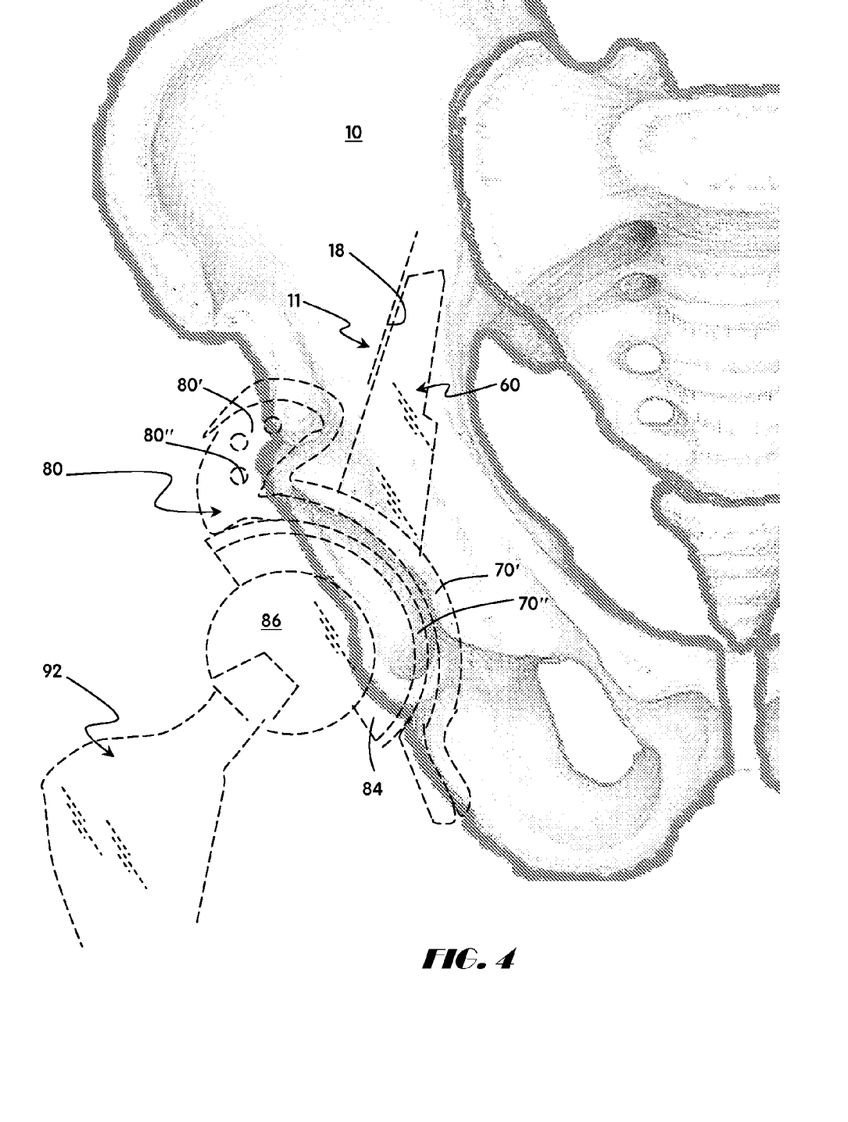
FIG. 4 is a frontal coronal view of a total reconstructed hip having an acetabular prosthesis according to one embodiment of the invention implanted using one or more of the methods shown in FIGS. 1a-2j.

FIG. 4 is a frontal coronal view of an acetabular prosthesis according to one embodiment of the invention implanted using method steps shown in FIGS. 1*a*-2*j*. After preparation of the iliac canal 11, a fixation implant 60 may be inserted and press-fit within the walls 18 of the canal 11. In the case shown in FIG. 4, the implant 60 is a porous augment. A first cement and/or bone graft material mantle 70' is then applied to the acetabular region 12 over top of, on the side of, or adjacent to portions of the implant 60. For example, medial morcelized bone graft may be placed against the augment 60.

An acetabular component 80, such as an acetabular cage (shown) is then applied over the first mantle 70'. Cage 80 may comprise one or more flanges 80' for stability and may further comprise one or more apertures 80' which serve as screw-mounting means or simply surfaces for interdigitation of bone cement and/or bone graft material mantle 70' for improved fixation. The acetabular cage 80 may be provided with a hood or buttress for added support to the liner 84 and/or the bone cement layer 70" bonding the liner 84 to the cage 80.

One or more additional acetabular components such as an acetabular liner 84 or acetabular shell may then be fixed to the cemented acetabular component 80. Fixation of the one or more additional acetabular components 84 may be facilitated by one or more second cement and/or bone graft material mantles 70" applied over the acetabular component 80. Either or both mantles 70', 70" may be substituted by one or more other fixation means including, but not limited to friction fit, screws, pegs, spikes, wires, bone matrix (e.g., mineralized and/or demineralized), cables, and clamps. In the particular example shown, an acetabular shell is not used, and instead, a liner 84 is fixed directly to the cage 80. However, an acetabular shell (82) may be employed between the cage (80) and the liner (84).

Figure 5A:
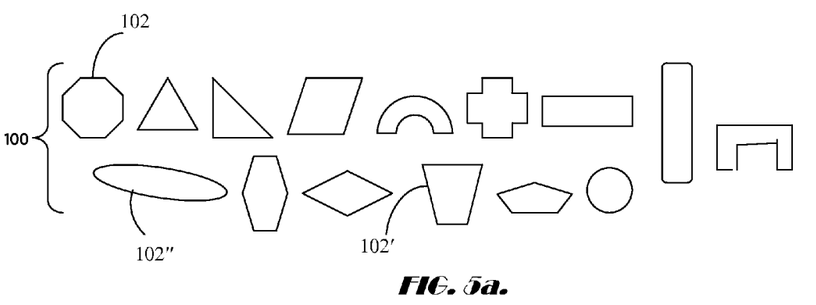
FIG. 5a. illustrates some examples of various cross-sectional profiles for the non-rotating means for ilium bone removal.

FIG. 5*a* illustrates some examples of various cross-sectional profiles for the non-rotating means for ilium bone removal. Non-rotating means for ilium bone removal such as rasps and broaches may comprise any number of geometric shapes. Geometric shapes may comprise one or more different cross-sections at various locations along their lengths. Peripheral profiles may include polygons such as octagons 102 and trapezoids 102', and may include curved or B-splined shapes 102".

Figure 5B:
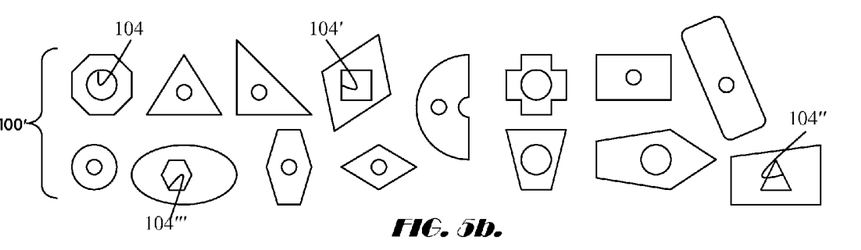
FIG. 5b. illustrates some examples of various cannulated cross-sectional profiles for the non-rotating means for ilium bone removal.

FIG. 5*b* illustrates some examples of various cannulated cross-sectional profiles for the non-rotating means for ilium bone removal. If guide rods 22 or reamers 30 are utilized, a central aperture extending through the length of the broaches may be employed to orient and guide the broach into the intramedullary canal 11 of the ilium 10. Said central aperture may have any cross-sectional shape capable of extrusion, including, but not limited to curved shapes such as circles and ovals 104, and polygons such as triangles 104", rectangles 104', and hexagons 104'".

Figure 6:
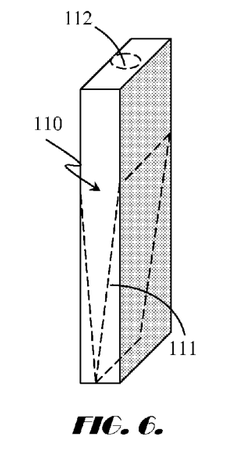
FIG. 6 is an isometric view of a distally converging tapered broach according to some embodiments of the present invention.

FIG. 6 is an isometric view of a distally converging tapered broach according to some embodiments of the present invention. Broach 110 may or may not be cannulated 112, and may comprise one or more converging surfaces 111 which may be planar.

Figure 7:
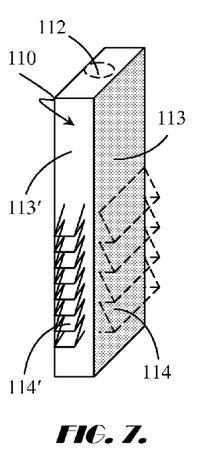
FIG. 7 is an isometric view of a broach according to some embodiments of the present invention having cutting surfaces thereon.

FIG. 7 is an isometric view of a broach according to some embodiments of the present invention having cutting surfaces thereon. Shown, is an acetabular broach 110, which may or may not be cannulated 112, and which may comprise smooth surfaces 113, 113' or cutting surfaces 114, 114' at portions. Cutting surfaces 114, 114' may be any known within the orthopaedic arts.

Figure 8:
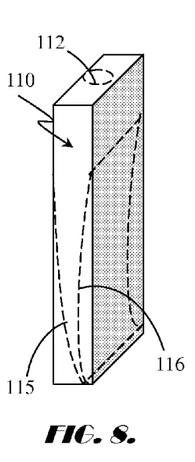
FIG. 8 is an isometric view of a distally converging curved and tapered broach according to some embodiments of the present invention.

FIG. 8 is an isometric view of a distally converging curved and tapered broach 110 according to some embodiments of the present invention. Broach 110 may have one or more converging surfaces 115, 116, at least one of which is curved in at least one plane.

Figure 9:
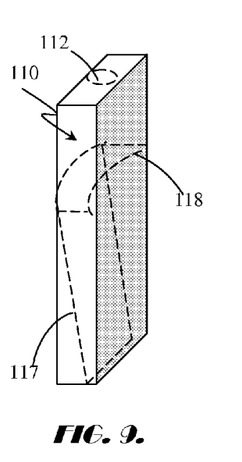
FIG. 9 is an isometric view of a curved and tapered broach according to some embodiments of the present invention.
Figures 10, 11:
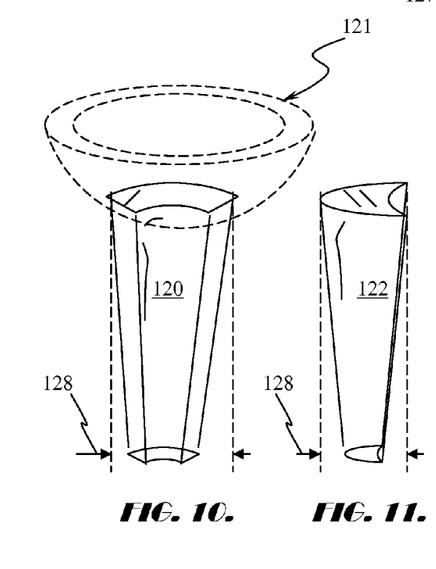
FIGS. 10-13 illustrate broach or rasp geometries according to some embodiments of the present invention.
Figures 12, 13:
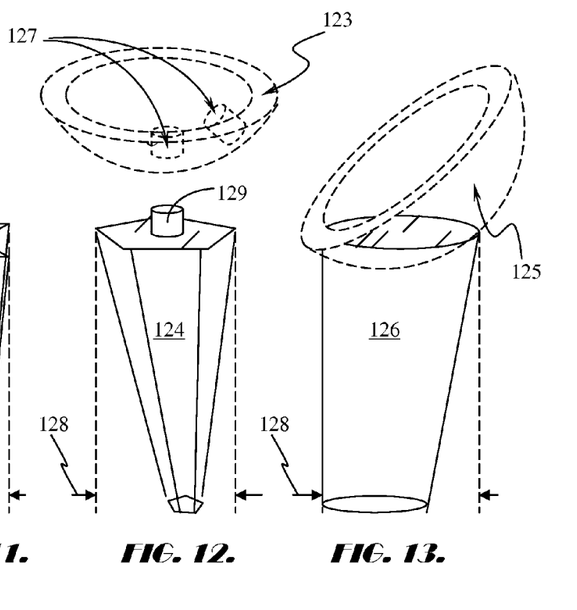

FIG. 9 is an isometric view of a curved and tapered broach 110 according to some embodiments of the present invention. Broach 110 may have converging surfaces 117, 118, at least one of which is curved in a transverse plane.

FIGS. 10-13 illustrate possible geometries for broaches, rasps, augments, and acetabular implant stems alike, according to some embodiments of the present invention. Shown, are non-radially symmetric geometries 120, 122, 124, 126 which may or may not have a distal geometry 128 which is smaller than a proximal geometry for easier insertion into a medullary canal of an ilium 10. Geometries 120, 122, 124, 126 may be eccentric or uniformly extruded having equal proximal and distal 128 geometries. Geometries 120, 122, 124, 126 may be provided for an augment alone 122, or may be provided to a stem 120, 126 of an integral acetabular implant 121, 125. Alternatively, geometries 120, 122, 124, 126 may be provided as a stem 124 for connecting to a separate acetabular implant 123 via connecting means 127, 129. Connecting means 127, 129 may comprise without limitation: cement, Morse tapers, press fits, threaded interfaces, male-female threaded connections, separate screw threaded into a boss, etc. Connecting means 129 may serve alternative uses, such a means for attaching or aligning other surgical instruments for preparing portions of the acetabular region.

Figure 14A:
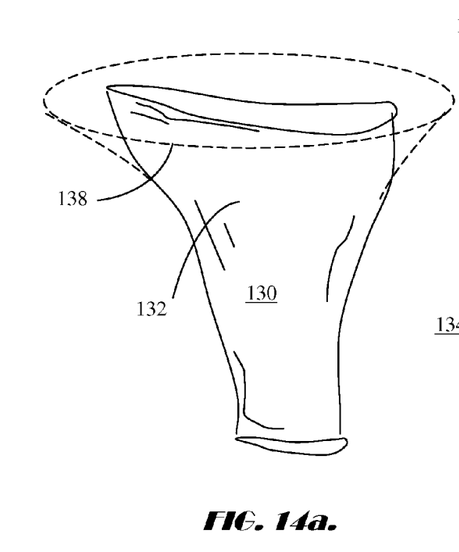
FIG. 14a. shows an example of an anatomically-shaped augment or trial for temporary or permanent implantation within an iliac canal on a first side of an ilium bone.

FIG. 14a. shows an example of an anatomically-shaped implant trial or augment 130 for implantation within an iliac canal on a first side of an ilium bone. Augment 130 may be a smaller portion of a larger implant 138 as illustrated by ghost lines. For example, augment 130, may have an integral flange to act as a cement buttress, or augment 130 may be a stem portion of an acetabular shell. It the embodiment shown in FIG. 14a, it is preferred that outer surface 132 of the augment 130 be designed to maximize cortical bone and/or cancellous bone interface between the augment 130 and the intramedullary canal 11 after the canal 11 is prepared. It is preferred that augment 130 is porous so that cement fixation is avoided; however, other surface textures are envisaged. For instance, if the augment 130 is to be used as a trial augment during trial reduction, the surface texture may be smooth for easy insertion and extraction.

Figure 14B:
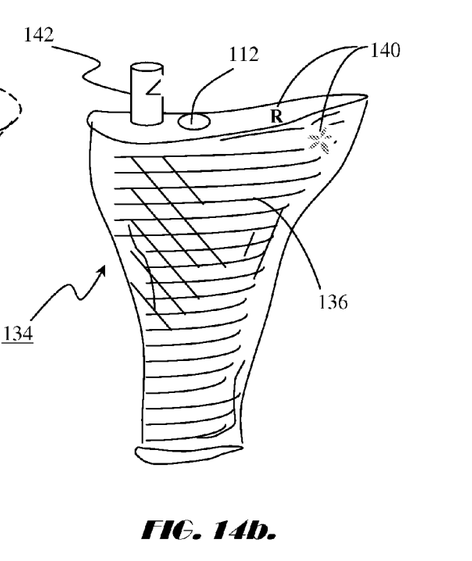
FIG. 14b. shows an example of an anatomically-shaped broach or rasp for preparing an iliac canal on a second side of an ilium bone which is different from the first side.

FIG. 14b. shows an example of an anatomically-shaped broach or rasp 134 for preparing an iliac canal 11 on a second side of an ilium bone which is different from the first side. Broach or rasp 134 may comprise indicia 140 which might convey information to the surgeon such as size, type, side of patient, serial number, manufacturer, etc. Broach or rasp 134 may be made integral with a broach handle 40 as shown in FIGS. 1c, 1e, 2c, and 2e, or may have a means for coupling 142 which allows the broach or rasp 134 to be removed from the broach handle 40. If a patient is scanned using radiant energy such as CT, MRI, or X-ray, a custom augment 130 and broach 134 may be provided to a surgeon to fill a specific defect.

Figure 15:
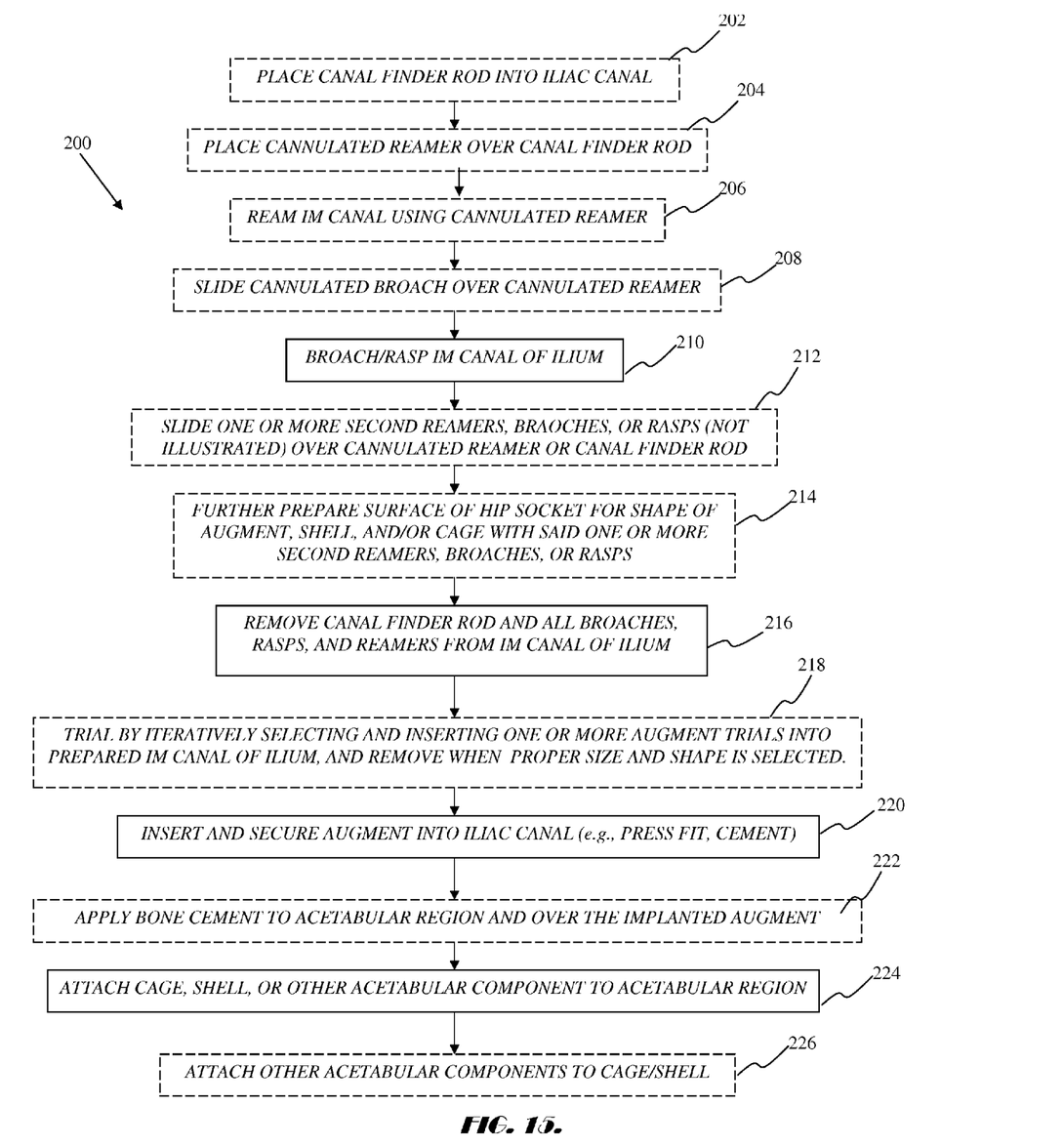
FIG. 15 is a schematic diagram illustrating method steps according to some embodiments of the present invention which use a reamer.

FIG. 15 is a schematic diagram illustrating method steps according to some embodiments of the present invention. In particular, FIG. 15 describes method steps shown in FIGS. 1a-1j. Optionally, step 202 is performed, where a surgeon places a canal finder guide rod 22 into the intramedullary canal 11 of the ilium 10. If the surgeon uses the canal finder guide rod 22, then a cannulated reamer 30 may be placed over the guide rod 22 in step 204. The intramedullary canal 11 is then reamed as necessary in step 206 to open up the canal 11 enough for broaching. Other surgical instruments may be attached to or extend from either the guide rod 22 or the reamer 30. The step of reaming 206 may be omitted or repeated using one or more different diametrically-sized reamers. After the intramedullary canal 11 of the ilium 10 is reamed 206, the last reamer 30 may be left within the canal 11 for use in a broaching step 210. The canal 11 is broached 210 and then the broach 44 is removed from the acetabular area 12. Broaching 210 may be substituted for other non-rotating means for removing bone material from the iliac canal 11 such as removing bone using osteotomes or impaction devices as discussed hereinafter. If the surgeon opts to use a guide rod 22 or reamer 30, the broach may be cannulated to serve as an alignment feature for alignment with respect to the guide rod or reamer and the step 208 of sliding the broach over the guide rod 22 and/or reamer 30 will be performed. If the guide rod 22 and cannulated reamer 30 are not used for surgery, the broach 44 need not be cannulated. Further preparation 212, 214 of an acetabular region 12 may be made by reaming over the guide rod 22 using larger diameter reamers at various depths to form one or more "countersinks" in the iliac canal 11, and/or by broaching surface portions of the acetabular region 12.

Once a suitable bone void 18 is created within the iliac canal 11 and/or surrounding iliac bone 10, some or all of the previously-inserted instrumentation (e.g., canal finder guide rod 22, reamers 30, broaches 44) may be removed from the acetabular region 12 in step 216 in order to facilitate trial reduction steps 218. It is not necessary to remove instrumentation 216 before trial reduction 218 if cannulated augment implants 60 and trial augments are used. In such cases, the trial augments and/or augment implants 60 are slid over the guide rod 22, reamers 30 or broaches 44 and the instrumentation is removed from the ilium 10 later in the surgical procedure. Trialing 218 while leaving the guide rod 22 or reamer(s) 30 in the canal 11 allows the surgeon to easily re-ream and increase trial augment size as needed for best fit and cortical engagement. The trial reduction step 218 is an optional step and may be omitted in cases when a correspondingly-sized and shaped broach becomes hard to remove.

When best size, shape, or fit is established, the one or more trial augments may be removed and one or more implant augments 60 are inserted in their place 220. Cement 70 can then be placed over the inserted augment 222, a cage 80 or other acetabular component (e.g., acetabular shell) attached 224 to the cement 70', and then a liner 84 or other acetabular component can be cemented 226 to the cage 80 or other acetabular component with a second cement layer 70". It should be noted that cement 70 may be replaced with friction, screws, or any other fixation means described herein.

For example, if the augment 60 to be inserted into the iliac bone 10 is a modular combination of different augments, or has an irregular or non-standard shape, one or more different broaches or modular interlocking/interchangeable broach segments (not shown) may be sequentially "stacked" to form a unique broach geometry complementary to the shape of the irregular or non-standard shape of the augment 60. Alternatively, steps 210 and 212 may be used in series progression with monolithic broaches having different shapes in order to create a bone void 18 having said irregular shape.

In another example, a surgeon may ream 206 over the guide rod 22, leave the reamer 30 in the intramedullary canal 11, broach 210 over the reamer 30 using a first broach 44, remove the first broach 44, broach a countersink into the intramedullary canal 11 and acetabular region 12 using a second broach (not shown), remove the second broach, and then round out the countersink formed by the second broach using a hemispherical reamer (not shown) to form a frusto-spherical countersink portion in the ilium bone 10.

Figure 16:
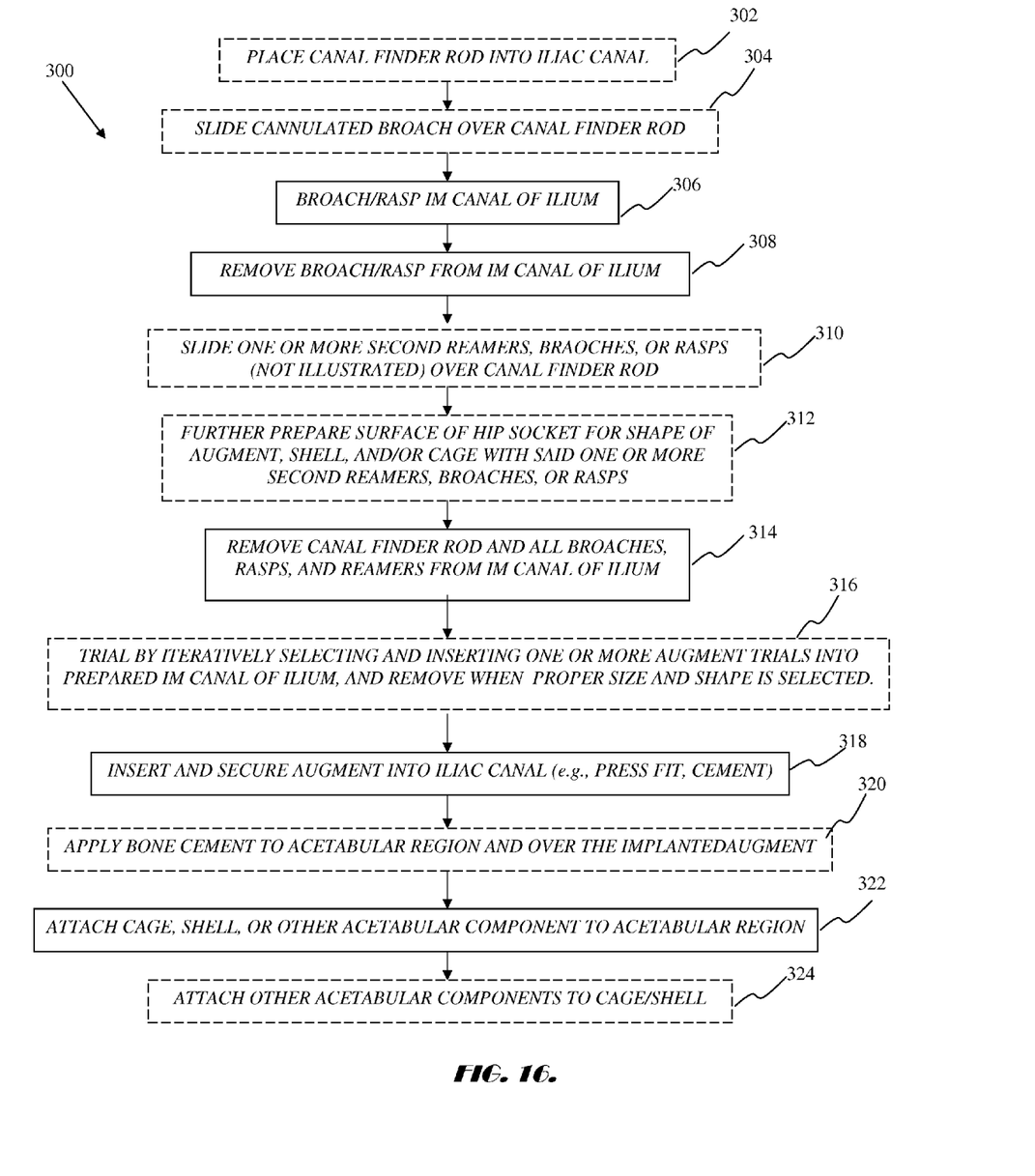
FIG. 16 is a schematic diagram illustrating method steps according to some embodiments of the present invention.

FIG. 16 is a schematic diagram illustrating method steps according to some embodiments of the present invention. In particular, FIG. 16 describes a method 300 of performing surgery as shown in FIGS. 2a-2j. Optionally, step 302 is performed, where a surgeon places a canal finder guide rod 22 into the intramedullary canal 11 of the ilium 10. If the surgeon uses the canal finder guide rod 22, then a cannulated broach 44 is placed over the canal finder rod in step 304 and then the canal 11 is broached 306. Other provided surgical instruments may be configured to attach to or extend from the guide rod 22. Broaching 306 may be substituted for other non-rotating means for removing bone material from the iliac canal 11 such as removing bone using osteotomes or impaction devices as discussed hereinafter. One or more cannulations on the broach 44 generally serve as an alignment feature for alignment with respect to the guide rod 22 during step 304. If the guide rod 22 and broach 44 is splined or keyed, it will facilitate different radial orientations of the broach 44 relative to the ilium during impaction 50 for best bone fit. If the guide rod 22 is not used for surgery, the broach 44 need not be cannulated. Once broaching 306 is finished, the broach 44 is removed 308 from the acetabular area 12. Further preparation 310, 312 of an acetabular region 12 may be made by reaming over the guide rod 22 using reamers at various depths to form one or more "countersinks" in the iliac canal 11, and/or by broaching surface portions of the acetabular region 12. One or more trialing steps using augment trials may be performed at any time during the procedure, particularly during or after broaching steps 1c-1e, 2c-2e or reaming step 1b and prior to final augment 60 implantation. Trials may be shaped and sized according to the augment to be implanted, however, are preferably formed without the high friction or porous outer surface used on the augment to be implanted for easy insertion and removal from ilium bone.

For example, if the augment 60 to be inserted into the iliac bone 10 is a modular combination of different augments, or has an irregular or non-standard shape, one or more different broaches or modular interlocking/interchangeable broach segments (not shown) may be sequentially "stacked" to form a unique broach geometry complementary to the shape of the irregular or non-standard shape of the augment 60. Alternatively, steps 310 and 312 may be used in series progression with monolithic broaches having different shapes in order to create a bone void 18 having said irregular shape.

In another example, a surgeon may broach 306 over the guide rod 22 using a first broach 44, remove the first broach 44, broach a countersink into the intramedullary canal 11 and acetabular region 12 using a second broach (not shown), remove the second broach, and then round out the countersink formed by the second broach using a hemispherical reamer (not shown) to form a frusto-spherical countersink portion in the ilium bone 10.

Once a suitable bone void 18 is created within the iliac canal 11 and iliac bone 10, all instrumentation (e.g., canal finder guide rod 22, reamer(s) 30, and broach(es) 44) is removed from the acetabular region 12 in step 314. Trialing with a trial acetabular implant such as an augment trial may be inserted into the void 18 to ensure proper fit and stability. The acetabular implant 60 (e.g., augment) is then inserted and fixed within the void 18 of the prepared iliac canal 11 in step 316. Subsequent acetabular components 80, 82, 84, 86 may then be attached to the acetabular region 12 as shown in steps 318, 320, and 322 using any of the means disclosed herein.

The term "augment" as used herein, may comprise without limitation, one or more of the following: a "porous bone-ingrowth structure", a "porous, reticulated, open-cell network", a "biocompatible metal foam", a "ceramic foam" (e.g., porous hydroxyapatite), a "polymeric foam" (e.g., porous PEEK, porous UHMWPE), a "trabecular construct", a "porous surface-texture" (e.g., a porous layer created by blasting or etching), a "solid substrate having a porous outer layer", a "device having a porous coating of at least one sintered powder(s)", a "porous sintered powder construct" (e.g., porous sintered spherical and/or asymmetric particles), "flame-sprayed metal" (e.g., flame-sprayed titanium), "plasma-sprayed metal" (e.g., plasma-sprayed titanium), a "non-porous construct" (e.g., block of polymeric, metallic, or ceramic material or the like), or porous allograft. It is anticipated that one or more "bio-active" treatments like HA may be applied to one or more augments.

It is understood that the non-rotating means for bone removal may comprise instruments other than broaches and rasps. For example, osteotomes (e.g., box osteotomes), punches, cutting blades (e.g., reciprocating saw blades or oscillating saw blades), impaction grafting tools, flexible cutting tools (e.g., flexible reamers or flexible drills similar to those used to insert dome screws through an acetabular cup), curved awls (e.g., devices that are rotated back and forth and 'oscillate' by hand), hand-reamers, tapered reamers, non-tapered reamers, non-cannulated T-handle intramedullary devices (e.g., Charnley awls or an intramedullary rods used for alignment in knee replacement), curved curettes, handheld burrs, reamers (cannulated or non-cannulated), and vibratory cutting tools may all be used in combination with or in lieu of broaches and rasps.

Figure 17:
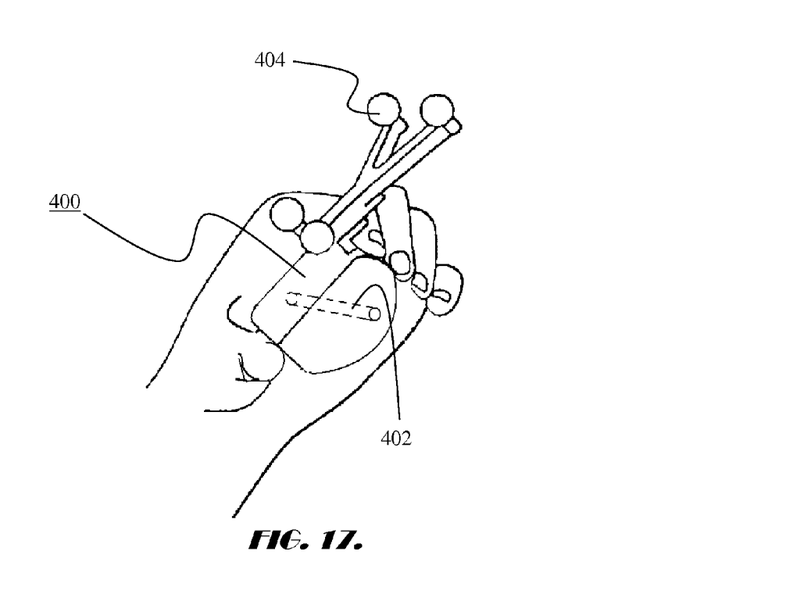
FIG. 17 is a jig for inserting a canal finder rod which may be advantageously utilized with computer-assisted surgery (CAS) systems.

Since some surgeons may find the canal 11 hard to locate, a jig 400 may comprise arrays and/or fiducial markers 404 as shown in FIG. 17 such that it may be used as a surgical instrument within a computer-assisted surgery (CAS) system (not illustrated). The CAS system is used to facilitate the spatial orientation of the jig 400 relative to the ilium 10 to ensure accurate placement of the guide rod 22 in the intramedullary canal 11. Once the jig 400 is correctly placed, it may be pinned to the ilium (pin holes not illustrated) or held in place by friction while the guide rod 22 is inserted through portal 402. Portal 402 serves as a guiding surface for the guide rod and may comprise a slit, slot, sliding surface, or aperture, so long as the portal 402 is sized and shaped for complimentary engagement with the guide rod 22. Is to be noted that multiple cross-sectional geometries for both the guide rod 22 and portal 402 are envisioned. It is also contemplated that the portal 402 may serve equally well as a guide for a cutting guide such as a rasp, broach, cutter, mill, or reamer.

Figure 18:
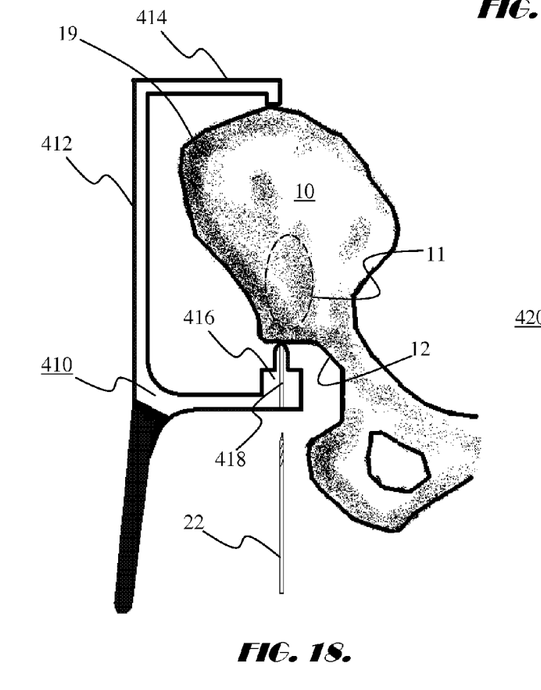
FIG. 18 is a jig for inserting a canal finder rod according to some embodiments.

Alternatively, a jig 410 such as the one shown in FIG. 18 may be used. The jig 410 is configured to guide a pin or guide rod 22 into the iliac canal 11. The jig 410 comprises an outrigger device 412 and a bottom portion 416 having a portal 416 therein. The bottom portion 416 is placed into the acetabulum 12 adjacent the superior dome. A top portion of the jig 414 is placed on the iliac rim, about 3 cm posterior to the ASIS 19, which is typically where the IM canal 11 extends.

Figure 19:
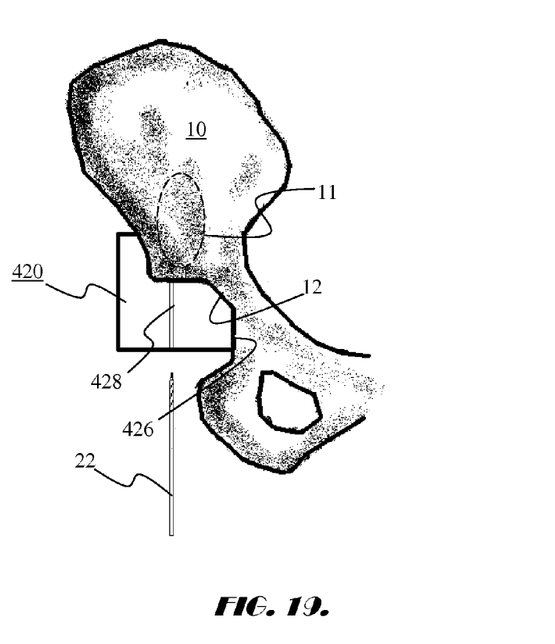
FIG. 19 is a jig for inserting a canal finder rod according to other embodiments.

Moreover, CT scans and pre-operative computer modeling methods may reveal iliac voids 11 which can be filled with one or more augments 60 for fixation. A patient is scanned using conventional X-ray or computer tomography (CT, MRI) methods. Data obtained from the scan (e.g., *.DICOM file format) is pre-processed with software (e.g., MIMICS by Materialise) and then uploaded to appropriate modeling software (e.g., Unigraphics/NX, CATIA, AutoCAD, Pro/Engineer, SolidWorks, etc) to create a 3D digital CAD model of the patient's ilium 10 and/or acetabular region 12. The iliac canal 11 of the patient is measured and quantified, and a patient-specific augment 60 may be manufactured to optimally fit the patient. The 3D digital model may also be used to create a custom patient-specific block 420 which has a surface 426 contoured to a portion of the patient's acetabular region 12. Said patient-specific block 420 further comprises a portal 428 which is configured to guide a canal finder pin or rod 22 into the iliac canal. The contoured surface 426 serves as a means for spatially locating the portal 428 relative to the patient's bone 10 for optimal location of the canal finder rod 22. As stated above, it is also contemplated that the portal 402 may serve equally well as a guide for a cutting guide such as a rasp, broach, cutter, mill, or reamer.

Alternatively, the iliac canal 11 may be identified for placement of the canal finder rod 22 without a jig 20, 400, 410, 420. This can be done by finding a thick portion of the ilium bone 10 extending from the superior acetabulum 12 to the iliac wing by palpating along the iliac crest to find the canal 11, so long as the patient is not too obese.

Acetabular implants 60 as described herein may be press-fit within the iliac canal 11. In some instances, the inventors have actually reduced the invention to practice with a #7 trabecular metal augment manufactured by Zimmer, Inc. of Warsaw, Ind. However, it should be known that any augment 60 suitable for implanting within the intramedullary canal of the ilium 10 may be utilized. Trialing with an augment trial (not shown) having a generally similar size and shape characteristics as the implant 60 to be implanted should be performed, in order to ensure good cortical engagement and stability.

It should be noted that the methods disclosed in this specification provide a surprisingly easy method of establishing remarkably good fixation and a stable superior buttress to cement a cage over the augment. Since no screws are needed during the operation with the present invention, the integrity of surrounding bone is preserved, and operating time is reduced. It has been observed by the inventors that intramedullary fixation using an augment as disclosed herein is clearly better than any type of screw fixation.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. For instance, if bone quality is poor, the step of inserting a guide rod and/or the step of reaming may not be necessary prior to broaching. Thus, the breadth and scope of the present invention should not be limited by any of the above-described exemplary embodiments, but should be defined only in accordance with the following claims appended hereto and their equivalents.

What is claimed is:

1. A method for performing an acetabular arthroplasty in an acetabulum of an ilium including an iliac ridge, the method comprising the steps of:
    locating an iliac canal of the ilium, the iliac canal extending along an axis from a surface of the acetabulum generally toward a portion of the iliac ridge;
    impacting a non-rotating bone removal tool aligned along the axis of the iliac canal, the impacting of the non-rotating bone removal tool removing bone within the iliac canal and forming a bone void along the iliac canal;
    securing a fixation implant within the bone void; and
    installing an acetabular implant within the acetabulum over the fixation implant.

2. The method of claim 1, wherein the locating step further comprises the step of cannulating the iliac canal to form a cannula in the iliac canal; and
    wherein the impacting comprises impacting the non-rotating bone removal tool along the cannula to form the bone void along the iliac canal.

3. The method of claim 2, wherein the locating step further comprises positioning a canal finding jig over the ilium.

4. The method of claim 3, wherein the canal finding jig comprises a first portion, a second portion and an alignment guide, the positioning of the canal finding jig comprises the steps of positioning the first portion of the canal finding jig against a portion of the acetabulum, and positioning the second portion of the canal finding jig against a portion of the iliac ridge and aligning the alignment guide along the axis of the iliac canal.

5. The method of claim 1, wherein the impacting step further comprises forming the bone void adjacent to cortical bone.

6. The method of claim 5, wherein the impacting step further comprises impacting a plurality of non-rotating bone removal tools to form the bone void adjacent to the cortical bone.

7. The method of claim 5, wherein the impacting step further comprises impacting a plurality of differently sized non-rotating bone removal tools to form the bone void adjacent to the cortical bone.

8. The method of claim 1, wherein the securing step further comprises the step of cementing the fixation implant into the bone void.

9. The method of claim 1, wherein the installing of the acetabular implant comprises attaching the acetabular implant to the fixation implant after the securing of the fixation implant within the bone void.

10. A method for performing an acetabular arthroplasty in an acetabulum of an ilium including an iliac ridge, the method comprising the steps of:
    locating an iliac canal of the ilium by positioning a canal finding jig over the ilium, the iliac canal extending along an axis from a surface of the acetabulum generally toward a portion of the iliac ridge; the canal finding jig comprising a first portion, a second portion and an alignment guide; the positioning of the canal finding jig comprises the steps of positioning the first portion of the canal finding jig against a portion of the acetabulum, and positioning the second portion of the canal finding jig against a portion of the iliac ridge and aligning the alignment guide along the axis of the iliac canal;
    impacting a non-rotating bone removal tool aligned along the axis of the iliac canal, the impacting of the non-rotating bone removal tool removing bone within the iliac canal and forming a bone void along the iliac canal and adjacent to cortical bone;
    securing a fixation implant within the bone void; and
    installing an acetabular implant within the acetabulum over the fixation implant.

11. The method of claim 10, wherein the locating step further comprises the step of cannulating the iliac canal prior to the step of positioning the canal finding jig over the ilium.

12. The method of claim 10, wherein the impacting step further comprises impacting a plurality of non-rotating bone removal tools to form the bone void adjacent to the cortical bone.

13. The method of claim 10, wherein the impacting step further comprises impacting a plurality of differently sized non-rotating bone removal tools to form the bone void adjacent to the cortical bone.

14. The method of claim 10, wherein the acetabular implant is selected from the group consisting of an acetabular cup and an acetabular cage.

15. A method for performing an acetabular arthroplasty in an acetabulum of an ilium including an iliac ridge, the method comprising the steps of:
- locating an iliac canal of the ilium, the iliac canal extending along an axis from a surface of the acetabulum generally toward a portion of the iliac ridge;
- aligning a non-rotating bone removal tool along the axis of the iliac canal;
- impacting the non-rotating bone removal tool, the impacting removing bone from the iliac canal and forming a bone void along the iliac canal; and
- securing a fixation implant within the bone void.

16. The method of claim 15, further comprising the step of installing an acetabular implant within the acetabulum over the fixation implant, the installing of the acetabular implant comprises attaching the acetabular implant to the fixation implant after the securing of the fixation implant within the bone void.

17. The method of claim 15, wherein the locating step further comprises cannulating the iliac canal to form a cannula in the iliac canal; and
- wherein the impacting comprises impacting the non-rotating bone removal tool along the cannula to form the bone void along the iliac canal.

18. The method of claim 15, wherein the locating step further comprises positioning a canal finding jig over the ilium; and
- wherein the canal finding jig comprises a first portion, a second portion and an alignment guide, the positioning of the canal finding jig comprises the steps of positioning the first portion of the canal finding jig against a portion of the acetabulum, and positioning the second portion of the canal finding jig against a portion of the iliac ridge and aligning the alignment guide along the axis of the iliac canal.

19. The method of claim 15, wherein the impacting step further comprises forming the bone void adjacent to cortical bone.

20. The method of claim 19, wherein the impacting step further comprises impacting a plurality of differently sized non-rotating bone removal tools to form the bone void along the iliac canal.

21. The method of claim 15, wherein the non-rotating bone removal tool comprises a broach or rasp.

22. The method of claim 1, wherein the non-rotating bone removal tool comprises a broach or rasp.

* * * * *